(12) United States Patent
Chang

(10) Patent No.: US 10,646,675 B2
(45) Date of Patent: May 12, 2020

(54) OXYGEN MASKS

(71) Applicant: Alexander C. Chang, Los Angeles, CA (US)

(72) Inventor: Alexander C. Chang, Los Angeles, CA (US)

(73) Assignee: Alexander C. Chang, Los Angeles, CA (US)

( * ) Notice: Subject to any disclaimer, the term of this patent is extended or adjusted under 35 U.S.C. 154(b) by 930 days.

(21) Appl. No.: 14/815,412

(22) Filed: Jul. 31, 2015

(65) Prior Publication Data

US 2016/0030695 A1 Feb. 4, 2016

Related U.S. Application Data

(60) Provisional application No. 62/031,273, filed on Jul. 31, 2014.

(51) Int. Cl.
| | |
|---|---|
| *A61M 16/06* | (2006.01) |
| *A61M 16/08* | (2006.01) |
| *A61M 16/10* | (2006.01) |
| *A61M 16/04* | (2006.01) |
| *A61M 16/12* | (2006.01) |

(52) U.S. Cl.
CPC ......... *A61M 16/06* (2013.01); *A61M 16/0463* (2013.01); *A61M 16/0875* (2013.01); *A61M 16/1005* (2014.02); *A61M 16/107* (2014.02); *A61M 16/12* (2013.01); *A61M 2016/0661* (2013.01); *A61M 2202/0208* (2013.01); *A61M 2205/75* (2013.01); *A61M 2230/432* (2013.01)

(58) Field of Classification Search
CPC .......... A61M 16/0875; A61M 2205/75; A61M 16/06; A61M 16/00; A61M 16/0605; A61M 16/0616; A61M 16/0622; A61M 16/0666; A61M 16/0672; A61M 16/0677; A61M 16/08; A61M 16/0816; A61M 2016/0661; A61M 2202/0208; A61B 5/082; A61B 5/091; A61B 5/097; A62B 18/00; A62B 18/02; A62B 18/025
USPC .......................................... D24/110.1, 110.4
See application file for complete search history.

(56) References Cited

U.S. PATENT DOCUMENTS

| | | | | |
|---|---|---|---|---|
| 4,320,754 | A * | 3/1982 | Watson ................. | A61M 16/08 128/204.25 |
| 5,318,038 | A * | 6/1994 | Jackson ................. | A61B 5/085 600/529 |

(Continued)

OTHER PUBLICATIONS

Chang, et al. (2013) "Comparing lung oxygen delivery with three different high Fi02 masks." *Respiratory Therapy*, vol. 8(3):19-21, Jun.-Jul. 2013.

(Continued)

*Primary Examiner* — Joseph D. Boecker
(74) *Attorney, Agent, or Firm* — Harness, Dickey & Pierce, P.L.C.

(57) ABSTRACT

The present disclosure relates to an oxygen mask comprising: a mask body defining a cavity configured to be positioned over the mouth and nose of a patient, an oxygen port formed on the upper half of the mask body, an annular aperture formed on the mask body, and at least one vent port formed on the mask body, wherein each vent port is formed on the bottom half of the mask body in a manner that patient's exhaled gases are directed towards the vent port.

6 Claims, 7 Drawing Sheets

(56) References Cited

U.S. PATENT DOCUMENTS

| | | | | |
|---|---|---|---|---|
| 5,560,354 | A | * | 10/1996 | Berthon-Jones ...... A61M 16/06 128/204.18 |
| 6,792,943 | B2 | | 9/2004 | Kumar et al. |
| 7,004,163 | B2 | * | 2/2006 | Nashed ................ A61M 16/00 128/201.22 |
| 8,960,195 | B2 | | 2/2015 | Lehman .................. 128/206.28 |
| 9,186,474 | B1 | * | 11/2015 | Rollins, III ....... A61M 16/0605 |
| 9,629,975 | B1 | * | 4/2017 | Pedro ................ A61M 16/0683 |
| 9,782,555 | B2 | * | 10/2017 | Burk ................. A61M 16/0816 |
| 2003/0024533 | A1 | | 2/2003 | Sniadach |
| 2006/0196510 | A1 | * | 9/2006 | McDonald ........... A61M 16/06 128/206.21 |
| 2007/0006879 | A1 | * | 1/2007 | Thornton ............. A61M 16/06 128/203.29 |
| 2008/0245370 | A1 | * | 10/2008 | Kobziar .................. A62B 7/14 128/206.21 |
| 2011/0083670 | A1 | * | 4/2011 | Walacavage ......... A61M 16/06 128/205.12 |
| 2012/0216806 | A1 | | 8/2012 | Rookard et al. |
| 2012/0330111 | A1 | * | 12/2012 | Borody ............ A61M 16/0488 600/301 |
| 2014/0196726 | A1 | * | 7/2014 | Mallek ............. A61M 16/0816 128/861 |
| 2015/0119742 | A1 | | 4/2015 | Tse et al. |
| 2015/0217075 | A1 | * | 8/2015 | Nair ................... A61M 16/085 600/531 |
| 2016/0030695 | A1 | | 2/2016 | Chang |
| 2019/0038863 | A1 | * | 2/2019 | Chang .................. A61M 16/06 |

OTHER PUBLICATIONS

Cohen, et al., "TSE 'Mask' Improves Oxygenation in Deeply Sedated Patients with Nasal Cannula during Upper Endoscopy." *Anesthesiology* 107:A922, 2007. Poster Presentation at American Society of Anesthesiologists Annual Meeting, Oct. 2007, Chicago, IL.

Dumont, et al. (2002) "Using a reservoir nasal cannula in acute care." *Critical Care Nurse*, vol. 22(4):41-46, Aug. 2002.

Ely, et al. (2003) "Delivery oxygen to patients." *British Journal of Anaesthesia, CEPD Reviews*, vol. 3(2):43-45.

Reesor, E., (2013) "Replacing several single function oxygen delivery masks with a single multi-function device." *BLS Systems Limited*, pp. 1-12, Jul. 24, 2013.

Stich, et al. (2009) "Getting inspired about oxygen delivery devices." *Nursing*, pp. 51-54, Sep. 2009, www.nursing2009.com.

(2007) Guide to understanding oxygen conserving devices. "Oxygen Delivery Fundamentals." pp. 6-8.

International Search Report (ISR) from corresponding PCT Application No. PCT/US2016/014671, dated Oct. 18, 2016.

Written Opinion of the International Searching Authority from corresponding PCT Application No. PCT/US2016/014671, dated Oct. 18, 2016.

* cited by examiner

OXYGEN MASKS

CROSS-REFERENCE TO RELATED APPLICATIONS

This application claims the benefit of U.S. Provisional Application No. 62/031,273, filed on 31 Jul. 2014. The entire disclosure of the above application is incorporated herein by reference.

FIELD

The present disclosure relates to masks for facilitating the delivery oxygen to a patient. More particularly, it relates to an oxygen mask operative to define an oxygen reservoir that collects and stores the amount of oxygen available for a patient to breathe in while undergoing medical procedures.

BACKGROUND

This section provides background information related to the present disclosure which is not necessarily prior art.

Oxygen masks are connected to a source of oxygen that is delivered directly to the patient's airway, namely, the nose and mouth. Conventional oxygen masks generally cover the entire nose and mouth areas and have no apertures to allow surgical tools to access the mouth or nose. Notwithstanding the ability of conventional masks to form a seal about the patient's airway, and attempt to confine the area about the airway to which oxygen is delivered, conventional masks suffer from numerous drawbacks. In particular, most conventional oxygen masks have a tendency to dilute the oxygen being delivered to the patient. Also, those masks cause oxygen to be dispersed about and away from the patient's airway, which can lead to ineffective oxygen delivery.

Nasal cannulation can be deployed to compensate for the patient's inability to breathe through his or her mouth. However, this approach has problems. For example, nasal cannulation delivers oxygen typically ineffectively and wastefully. The structure and function of most conventional oxygen masks assume that the patient undergoing the procedure will breathe in oxygen precisely as delivered. Additionally, this approach assumes that infusing sufficiently large volumes of oxygen will, in fact, ultimately reach the patient. The logic is flawed. Due to the dilution and dispersion of the oxygen being delivered by conventional masks, this practice is extremely wasteful. Attempting to deliver oxygen in the aforementioned manner wastes considerable amounts of oxygen that must be constantly delivered throughout the entire respiratory cycle. Only a very small portion of the oxygen is delivered to the patient.

In an attempt to address the foregoing issues, a specific type of oxygen mask/delivery system has been developed that essentially deploys a "face tent". After the patient assumes the lateral decubitus or prone position, a plastic sheet or bag is used to cover the patient's face, following nasal cannulation. The plastic sheet or bag is operative to define a tent over the airway that maintains a reservoir of oxygen supposedly made available to the patient. These modified oxygen masks, often referred to as the TSE mask, has been discussed in Shaul Cohen, et al., "TSE 'Mask' Improves Oxygenation in Deeply Sedated Patients with Nasal Cannula during Upper Endoscopy." *Anesthesiology* 107:A922, 2007. Poster Presentation at American Society of Anesthesiologists Annual Meeting, October 2007, Chicago, Ill.

The TSE mask is designed to improve effectiveness at inhibiting oxygen desaturation. First, the oxygen reservoir of the TSE mask can provide an inspiratory fraction of oxygen of 40-60% with oxygen flows of 4 L/min. Accordingly, titrating intravenous sedatives after pre-oxygenation can achieve moderate-to-deep sedation while maintaining spontaneous respiration without oxygen desaturation. Second, the patient's respirations are monitored with capnography or a pediatric precordial stethoscope placed over the trachea. Thus, if the patient becomes apneic because of airway obstruction or over-sedation, medical personnel still have an average of two to three minutes to manipulate the airway before oxygen desaturation occurs.

Furthermore, conventional masks are typically ill-suited for use in upper endoscopy procedures that require the surgical instrumentation be deployed through the mouth and throat of the patient. For example, conventional masks do not include a sufficient aperture to allow surgical tools to access the mouth or nose. In this regard, the oxygen mask needs to effectively deliver oxygen, while having an opening or orifice through which surgical instrumentation can be deployed. The opening or orifice in the mask must have enough flexibility to enable the instrumentation to be easily and readily manipulated, as occurs when instrumentation is deployed in upper endoscopy procedures.

In attempt to introduce an oxygen mask suitable for allowing surgical tools to access the mouth and nose during upper endoscopy procedures, a specific type of oxygen mask/delivery system has been developed. These surgical masks, often referred to as the Panoramic Oxygen Mask ("POM") has been discussed in U.S. Pat. No. 8,960,195 to Lehman. U.S. Pat. No. 8,960,195 describes an intubation-facilitating oxygen mask that can be worn during standard oxygen therapy. This mask is intended to provide for increased oxygen saturation and continuous monitoring of carbon dioxide of expired gases. This mask introduces an aperture in the mask above the mouth to allow surgical tools to access the mouth and nose during upper endoscopy procedures.

Although some conventional masks are designed for upper endoscopy procedures, these conventional masks still present health risks. For example, conventional masks designed for upper endoscopy procedures provide sub-optimal monitoring of patients. In 80% or more cases when patients are sedated, an anesthesiologist may not be present in the procedure room. In such situations, nurses generally monitor the patient for oxygenation status and breathing status in addition to their normal workload (e.g., paper work, administration of medication, following orders from endoscopists or other physicians, securing agitated and/or thrashing patients). Indications of breathing can include: level of consciousness (e.g., spoken response to commands can determine the patient's level of consciousness), visual breathing signs, vital signs (e.g., blood pressure, heart rate), EKG, oxygen saturation (oximetry), and $CO_2$ levels. However, determining all of these indications can occur in dark conditions or settings with less light, which can reduce accurate monitoring of patient breathing and oxygenation statuses.

When conventional masks designed for upper endoscopy use nasal cannula for oxygen supplementation, an end tidal $CO_2$ machine is typically used to monitor breathing. To measure the oxygen condition of the patient, a finger monitor is typically used. However, these monitoring techniques are problematic. For example, the $CO_2$ monitoring machine uses the same or similar alarm when a negative occurrence is detected. Therefore, the alarm sound of the $CO_2$ monitoring machine will not specify to the caretaker whether the patient is breathing, $O_2$ saturation is low, or any other number of reasons that trigger the alarm. Further, the $CO_2$ monitoring machine does not indicate what caused the trigger. For example, if $O_2$ saturation is low, the caretaker still has to determine whether it was because the patient is breathing through the mouth or for some other reason. Each reason that can trigger the alarm can have a different appropriate response. If the patient has too little oxygen in the body, then the $O_2$ flow rate can be increased to provide more oxygen. If the patient's airway is obstructed, then the airway must be opened. Without knowing the cause of the alarm, caretakers must take time to identify the cause. In many cases, false alarms can be triggered by events such as the patient thrashing, further making it harder for caretakers to respond appropriately and disturbing the working environment. The net effect of the $CO_2$ monitoring techniques of conventional oxygen masks designed for upper endoscopy procedures is compromised patient safety.

Despite various attempts to improve upon other conventional masks, all conventional masks (including masks designed for upper endoscopy procedures) have one or more of the following safety and effectiveness related issues: air entrainment, re-breathing of mechanical dead space air, no effective sequential oxygen delivery system, wasting of oxygen (or other target gas or drug), ineffective monitoring of expired gases for early recognition of undesired events, bulkiness, and high cost.

It has been recognized that there is a substantial need for an oxygen mask that can more efficiently and effectively provide oxygen enriched gas to be more readily taken in by a patient's airway while the patient breathes while wearing the oxygen mask (e.g., while during surgery).

There is a further need for such an oxygen mask that can improve monitoring of patients undergoing upper endoscopy procedures for early detection and prevention of oxygen desaturation or other undesired events.

There is a further need for such an oxygen mask that can make available a reservoir of oxygen enriched air immediately adjacent the patient's airway upon the uptake of a breath by the patient to a degree greater than conventional oxygen masks.

Moreover, there is a need for such a mask that can continuously maintain an enriched source of oxygen as maintained in a reservoir immediately accessible to the patient's airway while at the same time consuming substantially less amounts of oxygen than prior art oxygen masks.

There is still a further need for such an oxygen mask that is of simple construction, easy to deploy, can be readily used with nasal cannulation, and can be utilized on patients undergoing upper endoscopy procedures such that instrumentation can be deployed through such mask with relative ease and flexibility.

SUMMARY

This section provides a general summary of the disclosure and is not a comprehensive disclosure of its full scope or all of its features.

In one embodiment, there is provided an oxygen mask comprising: a mask body defining a cavity configured to be positioned over the mouth and nose of a patient, an oxygen port formed on the upper half of the mask body, an annular aperture formed on the mask body, and at least one vent port formed on the mask body, wherein each vent port is formed on the bottom half of the mask body in a manner that patient's exhaled gases are directed towards the vent port.

In another embodiment, there is provided an oxygen mask comprising: a mask body defining a cavity configured to be positioned over the mouth and nose of a patient, an oxygen port formed on the upper half of the mask body, an oxygen storage tube directly coupled to the bottom half of the mask body, an annular aperture formed on the mask body, and a vent port formed on the oxygen storage tube, wherein the vent port is formed on the oxygen storage tube in a manner that patient's exhaled gases are directed towards the vent port.

Further areas of applicability will become apparent from the description provided herein.

DETAILED DESCRIPTION

Figure 1:
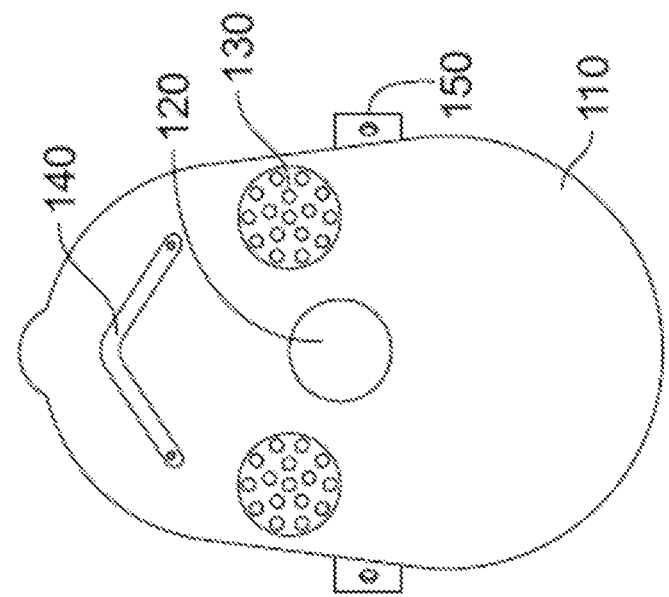
FIG. 1 shows a conventional simple face mask.
Figure 1:
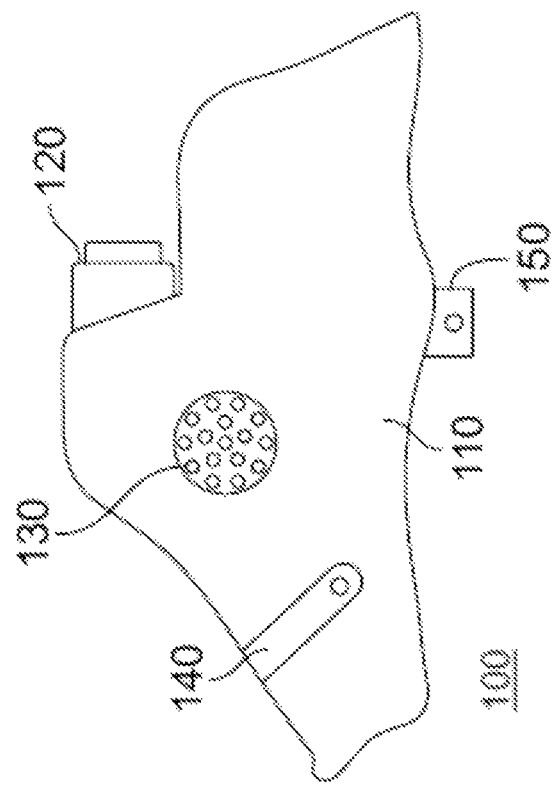

A multi-functional oxygen mask is provided for improving and controlling alveolar oxygen concentration. This can be achieved by strategically supplying oxygen in accordance to the respiratory cycle, which consists of three phases: expiration, expiratory pause (i.e., post expiration pause), and inspiration.

Conventional oxygen masks result in dilution of the intended oxygen (or other gas or drug) with significant amounts of room air during each inspiration, especially the early part of inspiration. In some instances, the intended therapy (e.g., oxygen, other gas, and drug) can be effectively reduced by half or more. This dilution occurs around the nasal area if a nasal cannula is utilized (and around the vent ports located near the nasal area if an open system mask such as a simple face mask or non-rebreathing mask is used) as the supplemental oxygen delivery device. Thus, patients do not receive the required or appropriate amount of oxygen or drug.

The oxygen mask of the present disclosure can provide at least the following benefits:

1. Improved Rescue Capability During Sedated Medical Procedures:

By increasing the oxygen reserves in the patient body during sedated upper endoscopic procedures, the oxygen mask of the present disclosure can prolong the safe period of apnea time from airway obstruction. Thus, caretakers will have extra time to resolve the airway problem. This extra time can be life-saving.

Additionally, the oxygen mask of the present disclosure provides a more sensitive $CO_2$ monitor that can result in fewer false alarms compared to vented open face masks or nasal cannula. The higher accuracy in detecting problems can allow better and earlier detection of problems. As is known, capnograms (wave form) are very important and must be deployed when a patient is under sedation for upper endoscope procedures. Capnograms tell whether a patient is breathing or not, and if there is no $CO_2$ waveform, it means there is no $CO_2$ on breathing (expiration). This usually means that there is an airway obstruction or that the patient is not breathing or may be over-sedated or that the heart is not pumping (i.e., cardiac arrest). It also indicates a slow-down in respiration due to over-sedation. It is the earliest detectable sign for highly undesirable events and an earlier signal than pulse oximeter.

The oxygen mask of the present disclosure can lessen dilution or dispersion of $CO_2$ compared to conventional masks (e.g., open airway masks) or nasal cannula alone. No (or substantially no) $CO_2$ accumulates on each breath with the oxygen mask of the present disclosure because $CO_2$ is pushed out of the oxygen mask by continuous oxygen flow during expiratory pause. Thus, there is no (or substantially no) $CO_2$ present during inspiration, and expired $CO_2$ will be less diluted and less dispersed during expiration because the oxygen mask of the present disclosure requires a lower oxygen flow. Since $CO_2$ is less diluted and dispersed, $CO_2$ monitoring is more sensitive and accurate.

By providing a mechanism that enables help to prevent or correct a blockage of the patient's air way to be more quickly and clearly identified, the oxygen mask of the present disclosure can enable caretakers to more promptly take appropriate action. For example, if a patient becomes apneic because of airway obstruction or over-sedation, the care team can still have a few to several minutes to manipulate the airway before oxygen desaturation occurs. This is due to the high efficacy of the oxygen mask of the present disclosure, which prolongs the safe period of apnea time.

2. Reduction of the Number of Misdiagnoses of Medical Conditions:

Conventional oxygen masks can lead to misdiagnosis or false alarms of medical conditions due to various problems (e.g., base line elevating due to rebreathing, less $CO_2$ due to dilution). These flawed masks cause false alarms which interfere with the work flow and there is a tendency to ignore most important monitoring. For example, an ineffective and inefficient oxygen and/or drug delivery system (e.g., because of air room dilution) can lead to an overestimation of the amount of oxygen the patient receives. In doing so, there can be an impression of a worse cardiopulmonary shunt than actually exists, potentiating the need for unnecessary invasive and expensive diagnostic procedures and therapies. However, by reducing or eliminating dilution of oxygen (or other intended therapy), the oxygen mask of the present disclosure can reduce faulty estimations of oxygen delivered to patients. This in turn can reduce misdiagnoses of medical conditions, thereby preventing unnecessary medical procedures which are sometimes risky and costly, for example, such as intubation.

3. Reduction or Elimination of Rebreathing of Exhaled Gases:

During expiration, fresh continuous oxygen flow pushes away exhaled gas (e.g., dead space gas, carbon dioxide) and any room air that may have entered the oxygen mask. These gases are pushed into the atmosphere through vent ports that are formed on the bottom half of the oxygen mask. After each expiration, there is an expiratory pause lasting approximately ⅓ of a respiratory cycle, during which no respiratory (expiration) air will flow. The fresh continuous oxygen flow continues to push away exhaled gas from the upper half of the oxygen mask to the bottom half. Exhaled gases and any room air that entered the oxygen mask are pushed out into the atmosphere until all or almost all exhaled gases are pushed out into the atmosphere.

4. Reduction or Elimination of Hypercarbia Occurrences During Oxygenation:

While pushing away the exhaled gas and any room air inside the oxygen mask, the fresh continuous oxygen fills a reservoir-like space inside of the oxygen mask between the nose area and vent port. In this manner, near 100% oxygen is collected and stored near the nose for immediate intake during the next inspiration. Thus, on inspiration, the patient inhales 100% or near 100% oxygen. Accordingly, hypercarbia is inhibited by virtue of no or insubstantial carbon dioxide being inhaled.

5. Reduction or Elimination of Oxygen Dilution with Room Air:

With conventional oxygen delivery devices, there is sudden make up tidal volume during each inspiration. This is especially true during the early part of inspiration when the peak inspiratory flow rate ("PIFR") occurs. With conventional oxygen delivery devices, a significant amount of room air flows into nose and dilutes the supplied oxygen during the PIFR time. This dilution occurs around the nasal area if a nasal cannula is utilized. If a vented oxygen mask is used, two (or sometimes one) ventilation ports on each side of mask near the nose area are responsible for the dilution during the active early phase of inspiration. Because of this early inspiration phenomenon, open or vented oxygen delivery system devices, such as the Venturi mask and high flow nasal cannula ("HFNC"), require high gas flows to avoid the effect of room air dilution. These devices can thus require 35 to 45 L/minute of gas flow for normal spontaneous respiration averaging 3 to 4 times of minute ventilation.

To avoid room air dilution, the oxygen mask of the present disclosure places each vent port to opposite top-or-bottom half from nasal area to create a gas reservoir between the nasal area and vent port(s). During each early part of inspiration, 100% oxygen that is stored during expiratory pause is breathed into the lungs first instead of diluted room air from the vent port(s), thereby avoiding (or delaying) PIFR effect with room air.

The basic physiological function of the PIFR is to enhance the velocity of air movement towards the alveolar to maximize effective and efficient oxygenation especially at the very early part of inspiration. Thus, any air dilution at the early part of inspiration can cause a lower fraction of inspired $O_2$, which runs against the purpose of the PIFR. The oxygen mask of the present disclosure can maximize the effect of the PIFR of any target gas or drug needed to be delivered from the reservoir to the lungs.

6. Reduction of Oxygen Wasting:

Conventional oxygen masks do not fully appreciate that the first half of inspiration is responsible (either fully or mostly) for alveolar oxygenation. It has been clinically observed that oxygen is absorbed into the blood essentially only during an early stage of inspiration in the breathing process. That is, it is during an early stage of inspiration that oxygen effectively reaches the alveoli. Oxygen applied during the latter stages of inspiration remains in "dead spaces" such as the pharynx, trachea, and bronchial tubes. Thus, approximately $\frac{1}{6}^{th}$ of the respiratory cycle is critical for alveolar oxygenation (early part of first half of inspiration). Hence, it has been observed and concluded that it is more advantageous to apply a greater volume of oxygen. Also, it is useful (and effective) to apply the oxygen only during an effective early stage of inspiration.

The effective early stage or peak inspiration flow rate time may only last for less than a second. For example, the effective early stage may last for approximately 0.2 to 0.3 seconds. In another example, the effective early stage may last for approximately 0.25 seconds. For most cases, the effective early stage is less than approximately one-quarter and usually approximately one-eighth of the duration of inspiration. Therefore, if oxygen were supplied at twice the normal volume per second rate (for example, 100 cc/s rather than 50 cc/s), a savings of more than one-half would be realized. In some cases, a savings of more than three-quarters would be realized.

Conventional oxygen masks are not capable of operating in accordance with this effective early stage inspiratory phenomenon. Thus, conventional oxygen masks are incapable of delivering 100% or close to 100% oxygen during the early stage of the first half of inspiration. Without any means for storing oxygen during expiratory pause, conventional oxygen masks waste oxygen that is continuous flowing (by sending the oxygen into the atmosphere) during these phases. Additionally, even during the first half of inspiration, much of the oxygen can be diluted with atmospheric air resulting in oxygen being wasted and/or being in low concentrations from the effect of the peak inspiration flow rate even during this most efficient phase. In some instances, less than 10% of continuous flowing oxygen is delivered to the alveolar during each breath.

The oxygen mask of the present disclosure can reduce wasting oxygen in at least two ways. First, by removing all or almost all non-oxygen gases (e.g., $CO_2$) from the oxygen mask between expiration and the end of expiratory pause, there may be no or insignificant air entrainment. Therefore, 100% (or near 100%) oxygen can be delivered to the alveolar during the early part of the first half of inspiration. Second, the oxygen mask of the present disclosure provides a reservoir in the oxygen mask to collect and/or store oxygen during expiratory pause. In doing so, continuously flowing oxygen can be retained even while the patient is not inhaling. Accordingly, wasting of fresh oxygen is reduced.

7. Improvement of Dosage Control:

The following properties can allow the oxygen mask of the present disclosure to improve dosage control:

1) No (or substantially no) air entrainment (no dilution with room air) during early inspiration;

2) 100% (or substantially 100%) oxygen first delivered to the alveolar via the Sequential Gas Delivery ("SOD") system; and 3) Ability to control oxygen amount (dosage) by adjusting the reservoir volume of the mask and oxygen flow rate. Conventional oxygen delivery devices rely on the promised accuracy of $FiO_2$ at the device level, not the alveolar level. The oxygen mask of the present disclosure can deliver, control, titrate, and maintain the desired proper oxygen amount (dosage) at the alveolar level.

In some cases, the continuous oxygen flow rate can be about 25 L/minute to about 75 L/minute. In other cases, the continuous fresh oxygen flow rate can be about 45 L/minute. By using such continuous fresh oxygen flow rates, the oxygen mask of the present disclosure can maintain efficiency in delivering oxygen to the user. In some cases, such flow rates can result in about 50 cc to about 300 cc that can be inhaled during the effective early stage. In other cases, such flow rates can result in about 150 cc to about 200 cc that can be inhaled during the effective early stage.

The volume of the reservoir can vary depending on the desired $O_2$ concentration. In some cases, the target $FiO_2$ can be from about 24 to about 60%. In other cases, the target $FiO_2$ can be from about 50 to about 100%. According to another embodiment, the reservoir varies from approximately 100 to 150 cc and the oxygen mask can store a total of up to approximately 400 cc via reservoir and attached oxygen storage tube. The storage volume and oxygen flow rate of the oxygen mask of the present disclosure can be adjusted to accommodate each patient. For example, the necessary storage volume can be calculated using the patient tidal volume ("TV"), respiratory rate, and target $FiO_2$. If the patient TV is 450 cc, respiratory rate is 20 L/min, and target $FiO_2$ is 100%, then the storage volume and oxygen flow rate can be calculated as follows:

Since ⅔ of TV goes to the alveolar, 450 cc×⅔=300 cc that goes to the alveolar. Thus, the total storage volume should be about 300 cc. If the oxygen mask of the present disclosure can store 150 cc in the mask body, then a connected oxygen storage tube can be adjusted to provide an additional 150 cc of storage volume. Next, the oxygen flow rate needs to be set to accommodate the entire respiratory cycle. Since 300 cc reflects only one third of the respiratory cycle (i.e., inspiration), 300 cc×3=900 cc is the total volume that needs to be delivered to the oxygen mask per respiratory cycle. If the patient has a respiratory rate of 20/minute, then 900 cc×20 L/min=18000 cc/min or 18 L/min should be the flow rate. Such flow rate is far lower than 35 to 45 L/min required by the high flow nasal cannula device for 100% $FiO_2$.

8. Improvement of Efficacy of Alveolar Oxygenation by Employing a Sequential Gas Delivery ("SGD") Pattern:

On inspiration, the oxygen that was saved or collected in the reservoir space during the expiratory pause, in addition to the continuously flowing oxygen provided to the mask, will be delivered to the alveoli in a SGD pattern. In this manner, 100% oxygen is first delivered, without dilution with room air or expired gases from dead space ventilation, at the most effective and efficient oxygen delivery time. In many cases, this time frame is the first about 0.2 to about 0.3 seconds of the early part of inspiration. This initial oxygen delivery is followed by make-up tidal volume which can comprise oxygen from the continuous oxygen flow with room air.

Thus, an oxygen mask of the present disclosure defines a reservoir for storing oxygen. According to an embodiment, the reservoir varies from approximately 20 cc to 100 cc. In an embodiment, the reservoir is approximately 75 cc. Volume can be changed depending on the design of the structure and the function of the mask for various different clinical applications. Oxygen is stored during expiratory pause from the upper area of the mask spread around the nose and is delivered as a bolus (approximately 20-100 cc out of 450 cc of normal breath volume) during inspiration. This early 20-100 cc of bolus of oxygen rich air will be inhaled to the alveolar effectively and efficiently where oxygen is exchanged.

In use, the oxygen mask of the present disclosure can be used in combination with nasal cannulation or another oxygen source whereby oxygen is delivered to the patient's nasal passages. Unlike conventional oxygen masks, the oxygen masks of the present disclosure are operative to define a reservoir which collects, holds and makes immediately available an oxygen enriched reservoir. This reservoir can be immediately adjacent the patient's airway. Oxygen in this reservoir can be immediately inhaled as the patient breathes during the medical procedure. In this regard, oxygen continuously fed via nasal cannula or other oxygen source will fill the reservoir defined by the mask during such time as the patient pauses between taking breaths.

The oxygen reservoir thus not only defines a reservoir of oxygen, it also selectively positions the oxygen directly about the patient's airway so that the patient can and must breath in the oxygen enriched air versus air where the supplemented oxygen is either diluted and/or is dispersed away from the nose and mouth of the patient when the patient uptakes air. In this regard, the oxygen mask of the present disclosure can maintain the same bolus that is readily accessible for every breath the patient takes in.

This is in contrast to conventional oxygen masks that deploy a constant flow of oxygen and air, only a portion of which is actually consumed at select moments (e.g., first ⅔ of first half of inspiration) when the patient breathes. For example, with a standard nasal cannula and conventional oxygen mask, the continuous flow of oxygen during patient exhalation is wasted to the atmosphere. However, the reservoir defined by the oxygen mask of the present disclosure is designed to store approximately 50 cc and up to 100 cc of oxygen. The storage volume depends on factors including, but not limited to, the respiratory rate of the patient and minute ventilation. A flow rate of 3 liters of oxygen per minute can maintain a bolus of highly concentrated oxygen between each breath. This feature helps reduce the effect of dilution/dispersion of gas by entrained room air at normal inspiratory rates. By virtue of the increased efficiency, as well as the subsequent benefits of more thorough oxygenation to the patient, a substantially higher degree of care can be provided.

Conventional masks containing a reservoir cannot achieve the above. For example, the TSE mask does provide a bag-like reservoir that is operative to contain some of the oxygen delivered to the patient, typically via nasal cannulation. Such tent-like structure still experiences sufficient dilution and dispersion of the oxygen delivered thereto, and does not position the oxygen immediately adjacent the patient's airway where the patient can uptake the oxygen. Moreover, such tent does not effectively save oxygen or remove expired gases to prevent dead space expired gases from being re-breathed during expiratory pause. Thus, the TSE mask is less efficient and not the standard for use by non-physician healthcare providers. Similar to the TSE mask, none of the other conventional oxygen masks can provide efficient oxygen by utilizing boluses of 100% or near 100% oxygen stored immediately adjacent to the patient's airway.

9. Improved Control of the Dosage of Oxygen (or Other Gas or Drug) Delivered to the Patient:

By adjusting the volume of oxygen stored in the reservoir during expiratory phase, the oxygen mask of the present disclosure can more accurately determine oxygen delivered to the alveolar.

10. Improved Preservation of Natural Water Vapor:

Water vapor can be collected and stored in a reservoir at least because the oxygen mask of the present disclosure can use a lower flow of oxygen. Benefits of preserving water vapor include preventing dry mouth, mucous plugging, and nasal mucosa drying.

11. Reduction of Costs in Producing the Oxygen Mask:

Conventional masks can use multiple one-way valves and/or reservoir bags that can result increased costs of production. The oxygen masks of the present disclosure can provide a full range of oxygen masks, including inexpensive masks. By not utilizing one-way valves and/or reservoir bags, oxygen masks of the present disclosure can reduce production costs. However, some oxygen masks of the present disclosure may incorporate one-way valves and/or reservoir bags.

The fundamental principles of the oxygen mask of the present disclosure can be utilized in a wide variety of applications (beyond upper endoscopy procedures) where more efficient delivery of oxygen to a patient is desired.

Exemplary embodiments will now be further described with reference to the Drawings.

Referring now to FIG. 1, a conventional oxygen mask, shown generally as reference number 100, is illustrated. As shown, conventional oxygen mask 100 comprises the following elements: a mask body 110, an inlet port 120, vent ports 130, a nose clip 140, and strap attachments 150. In conventional oxygen masks, the vent ports are generally formed near the nasal area of the conventional oxygen masks. For example, in the illustrated conventional oxygen mask, the vent ports 130 are formed on the upper half of the mask body 110. When the conventional oxygen mask 100 is worn, the vent ports 130 will be near the nasal area, oral area, or both.

FIGS. 2-7 illustrate oxygen masks embodying one or more aspects of the present disclosure. In general, the oxygen masks of the present disclosure can be lightweight, comfortable to wear, ergonomically shaped, and/or disposable.

Figure 2:
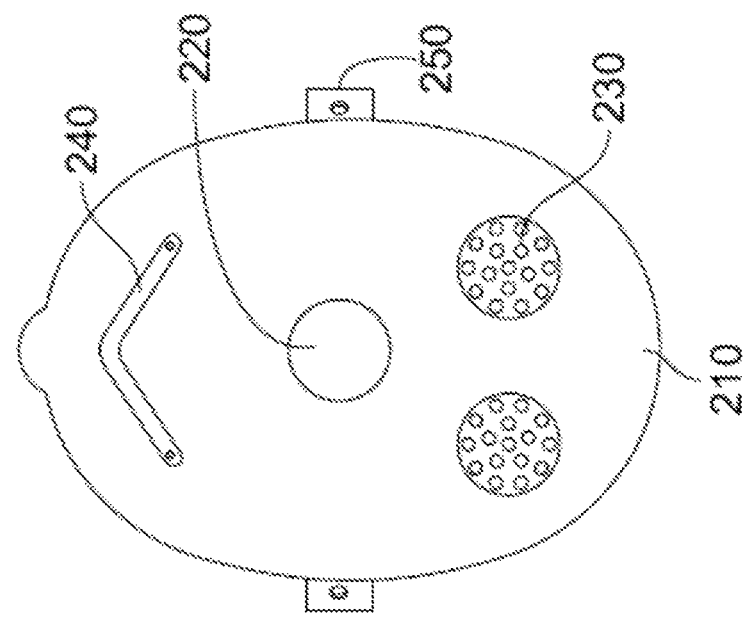
FIG. 2 shows an embodiment of a low $FiO_2$ mask in accordance with the present disclosure.
Figure 2:
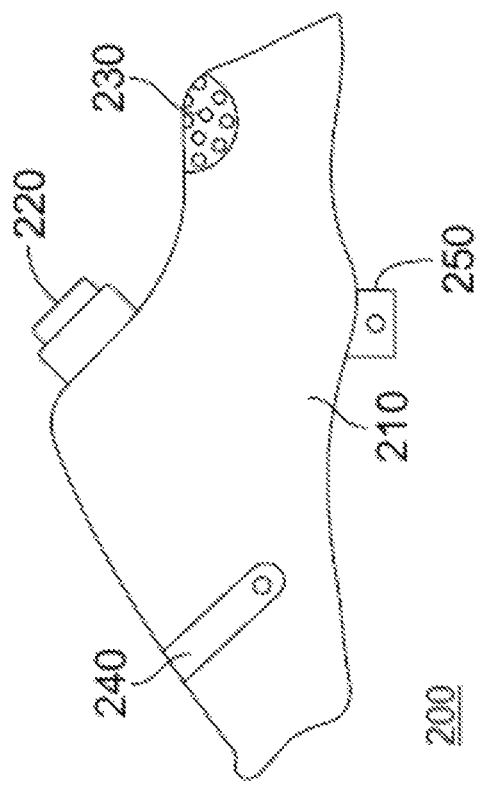

FIG. 2 illustrates an embodiment where the oxygen mask 200 includes a mask body 210, an oxygen port 220, vent ports 230, a nose clip 240, and strap attachments 250.

The generally concave mask body 210 is molded of a generally gas-impermeable material, such as non-toxic medical grade plastic polymer material. In an embodiment, the mask body 210 is made of silicone or polyvinyl chloride. The mask body 210 material can be transparent to allow clinicians to observe the patient's condition. The mask body 210 and connections and attachments thereto may be disposable.

The mask body 210 defines a cavity adapted to fit over the mouth and the nose of the patient. The peripheral edge of the mask body 210 is contoured so as to substantially seal against the surrounding facial tissue of the patient, to establish an inner chamber portion or inner-space. The peripheral edge can be any shape as long as it is contoured so as to substantially seal against the surrounding facial tissue of the patient. The peripheral edge may be formed to include one or more recesses to allow nasal cannula to access the inner-space.

In various embodiments, the mask body further comprises an interface (not pictured) which can be attached to the peripheral edge of the mask body 210 to inhibit an inner-space of the mask body from substantial contamination with room air when the oxygen mask is in use. The interface can be made of various materials including, but not limited to, cushion, padding, foam, and elastic.

The volume of the inner-space in accordance with present disclosure is generally smaller than those of conventional masks. The mask 200 is very efficient in delivering oxygen and thus does not require as much inner-space for oxygen storage (e.g., a reservoir) as required for conventional masks. In certain embodiments, the volume of the inner-space is about 25 to about 100 cc. Accordingly, the oxygen mask 200 can be configured to store about 25 to about 100 cc of oxygen when the oxygen mask 200 is worn. In a particular embodiment, the oxygen mask 200 is configured to store about 75 cc of oxygen when the oxygen mask 200 is worn.

The oxygen port 220 is configured to accept a standard oxygen tube. In various embodiments, the oxygen port 220 can be configured to accept any type of oxygen tube. The oxygen port 220 allows oxygen to flow from an oxygen source (not pictured) to the inner-space of the oxygen mask 200. The oxygen port 220 is formed on the upper half of the mask body 210. In an embodiment, the oxygen port 220 is formed right above the half-way line that separates the upper half and the bottom half of the mask body 220. In this manner, the oxygen port 220 is located around the nostrils of the patient when the oxygen mask 200 is worn allowing oxygen to be delivered to the nasal area.

One or more vent ports 230 are disposed on the bottom half of the mask body 210, allowing gases to be discharged from the oxygen mask. In various embodiments, the vent port(s) 230 are located between one and four inches from the bottom of the mask body 210, around three inches from the bottom of the mask body 210, or around two inches from the bottom of the mask body 210. In a particular embodiment, the oxygen mask 200 includes two vent ports 230. The vent ports 230 are disposed on opposite sides of the mask body 210. The vent ports are located on the mask body 210 such that they are below the patient's mouth when the oxygen mask 200 is worn.

The vent port(s) 230 may include perforations allowing free flowing of gases. The vent port(s) 230 may be formed integrally with the molded mask body 210 or may be inserted into the mask body 210.

The oxygen mask 200 may have an adjustable nose clip 240 disposed on the upper half of the mask body 210. In an embodiment, the adjustable nose clip 240 is disposed on the upper half of the mask body 210 such that the nose clip 240 is over the nose when the oxygen mask 200 is worn. The adjustable nose clip 240 can be adjusted to conform to the nose to stabilize the oxygen mask 200 in position on the patient's face. The adjustable nose clip 240 can be made of various flexible materials. In an embodiment, the adjustable nose clip 240 is made of metal.

The oxygen mask can include any number of strap attachments 250. In the illustrated embodiment, the oxygen mask includes two strap attachments 250. The two strap attachments 250 are disposed on opposing sides of the mask body 210 and are integrally molded with the mask body. In various embodiments, the strap attachments 250 can be separate pieces from the mask body and attached to the mask body through different means (e.g., adhesive, fasteners, and screws). The strap attachments 250 can include holes disposed thereon to allow straps to be attached to the strap attachments 250.

Figure 3:
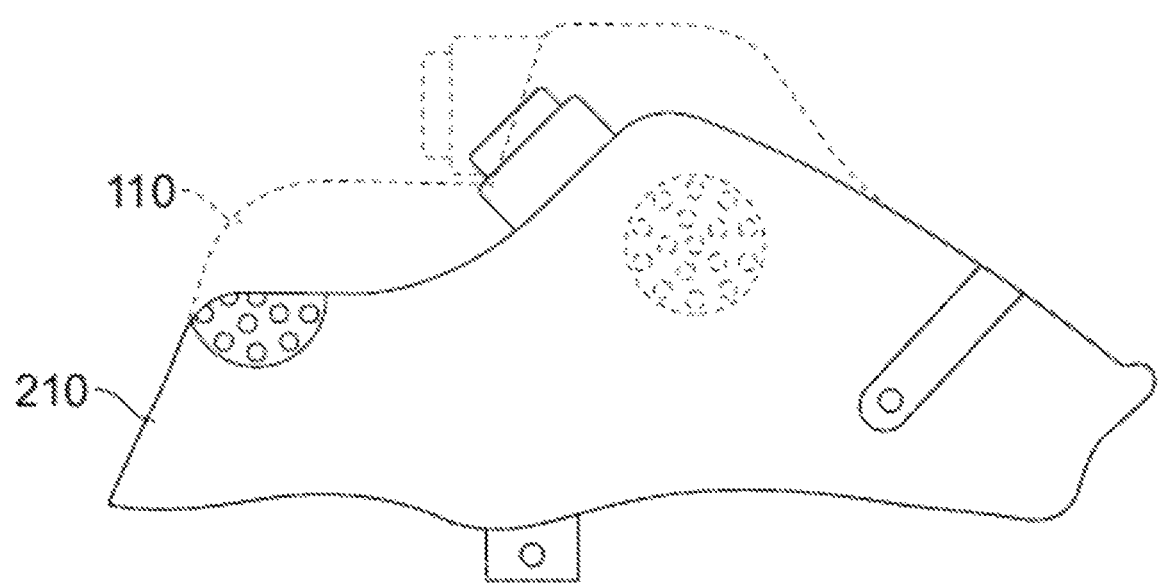
FIG. 3 illustrates comparison of a conventional mask, such as FIG. 1, and an embodiment of FIG. 2.

FIG. 3 shows a comparison of the conventional oxygen mask 100 shown in FIG. 1 and the oxygen mask 200 shown in FIG. 2. The conventional oxygen mask 100 is shown as the dashed lines, while the oxygen mask 200 is shown as the solid lines. Generally, the mask body 210 has a slimmer profile than the mask body 110 because the mask 200 does not need an much inner-space as that of the mask 100 due to its higher efficiency in oxygen delivery. The vent ports are placed differently in the two oxygen masks: the vent port(s) of oxygen mask 200 is disposed near the bottom of the mask on the mask body 210; whereas, the vent port(s) of the conventional oxygen mask 100 is disposed near the nasal area (or the central area) of the mask body 110.

Figure 4:
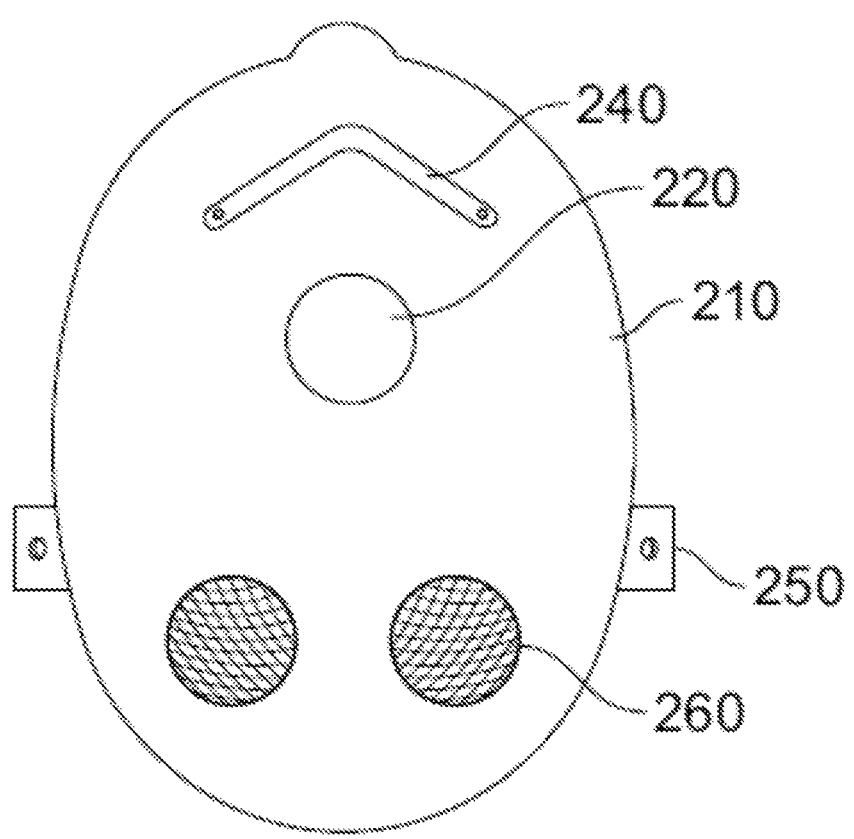
FIG. 4 shows the mask of FIG. 2 further comprising filters.

FIG. 4 illustrates another embodiment of the oxygen mask of FIG. 2. The oxygen mask 200 can optionally include filters 260, which can be placed over each vent port 230 or can be disposed on oxygen mask 200 instead of vent ports 230. The filter is designed to filter out various undesirable materials (such as pathogens).

Figure 5:
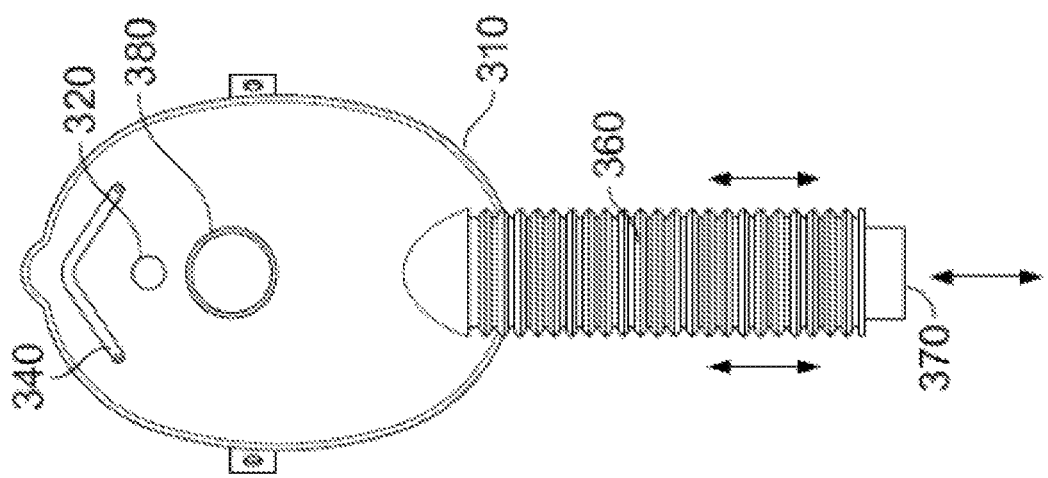
FIG. 5 shows an embodiment of a high $FiO_2$ mask in accordance with the present disclosure.
Figure 5:
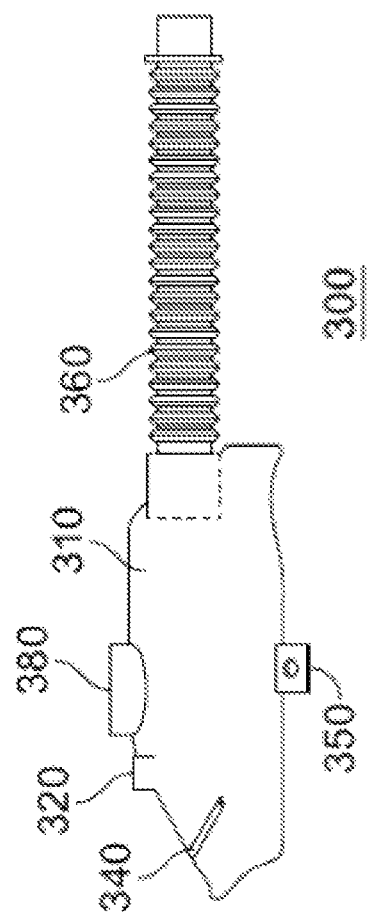

FIG. 5 describes another oxygen mask of the present disclosure shown as reference number 300. The oxygen mask 300 can include a mask body 310, oxygen port 320, nose clip 340, strap attachments 350, oxygen storage tube 360, vent port 370, and supplemental oxygen port 380. Nose clip 340 and strap attachments 350 are in accordance with other embodiments of the present disclosure.

The mask body 310 is as described above with the mask body 210.

The oxygen port 320 is as described above with the oxygen port 220.

The supplemental oxygen port 380 is formed near the central area or upper half of the mask body 310. The supplement oxygen port 380 can be configured to allow an oxygen source (not pictured) to connect to the supplemental oxygen port 380. In this manner, oxygen can be delivered via both the oxygen port 320 and supplemental oxygen port 380 to provide a higher $O_2$ concentration than oxygen were delivered only by oxygen port 320. The placement of the supplemental oxygen port 380 can allow oxygen to be directly delivered to the inner-space or carbon dioxide to be directly sampled from the inner-space. In an embodiment, the supplemental oxygen port 380 is formed right above the halfway line that divides the upper half and bottom half of the mask body 310. The supplemental oxygen port 380 can be any shape (e.g., generally circular, generally oval-shaped, generally rectangular), as long as the oral aperture can be formed on the mask body 310. The size of the supplemental oxygen port 380 can be between 0.1 inches and 3 inches in diameter (or by longest length). In an embodiment, the supplemental oxygen port 380 is circular in shape and about 1 inch in diameter. In an embodiment, the supplemental oxygen port 380 can be configured as an aerosol therapy port to allow aerosol units to be connected to the supplemental oxygen port 380. When supplemental oxygen port 380 is used for aerosol therapy, oxygen port 320 can be used to deliver oxygen directly to the inner-space.

The oxygen storage tube 360 may be formed integrally on the molded mask body 310 or may be attached to the mask body 310 through a connection hole in the mask body 310. The oxygen storage tube 360 is formed on or connected to the mask body 310 near the bottom of the mask body 310, for example, within three inches from the bottom of the mask body 310. In the illustrated embodiment, the oxygen storage tube 360 is attached to the mask body 310 within one inch from the bottom of the mask body 310. The oxygen storage tube 360 is adjustable and can be made of any gas-impermeable material, such as non-toxic medical grade plastic polymer material (e.g., silicone or polyvinyl chloride).

In an embodiment, the oxygen storage tube 360 can be corrugated as shown to allow adjustment of the length. By adjusting the length of the oxygen storage tube 360, the volume of the oxygen storage tube 360 can be increased and decreased. In an embodiment, the oxygen storage tube 360 is configured to have a volume correlating to about ⅔ the minute ventilation of the patient. The diameter of the oxygen storage tube 360 can be from about 0.5 inches to about 2.0 inches, or from about 0.75 inches to about 1.0 inches. The length of the fully-extended oxygen storage tube 360 can be from about 1 inch to about 36 inches, or from about 4 inches to about 16 inches. The length of the oxygen storage tube 360 can be adjusted according to patient size, lung capacity or one or more spirometry values. In the illustrated embodiment, the fully-extended oxygen storage tube 360 is about 12 inches in length.

The distal end of the oxygen storage tube 360 (opposed to the proximal end on the mask body 310) can include the vent port 370, allowing gases to flow from the oxygen storage tube 360 to the outer environment. In an embodiment, the oxygen storage tube 360 has a simple opening instead of the vent port 370. The location of the vent port 370 on the distal end of the oxygen storage tube 360 allows the vent port 370 to be located further away from the nasal and oral areas of the patient than the oxygen mask 200 illustrated in FIGS. 2-4. The vent port 370 may include perforations allowing free flowing of gases. The vent port 370 may be formed integrally with the oxygen storage tube 360 or may be inserted into the oxygen storage tube 360.

Figure 6:
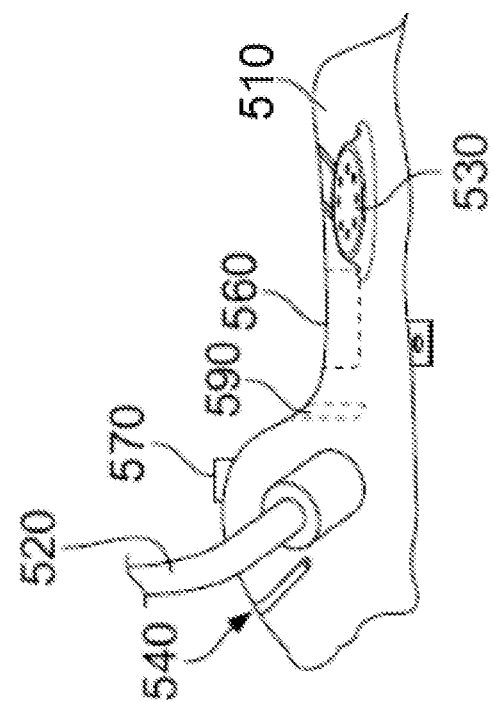
FIG. 6 shows an embodiment of an endoscopy mask in accordance with the present disclosure.
Figure 6:
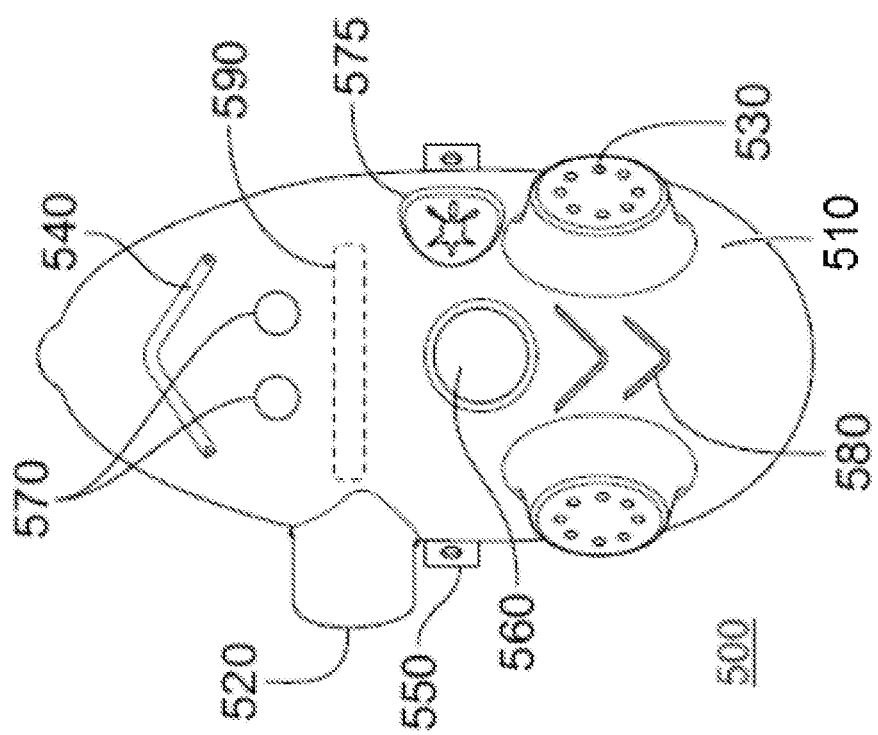

Now referring to FIG. 6, another oxygen mask of the present disclosure is shown as reference number 500. The oxygen mask 500 can include a mask body 510, oxygen port 520, vent ports 530, nose clip 540, strap attachments 550, oral aperture 560, nasal instrument ports 570, suction port 575, flexibility slits 580, and protrusion 590. The nose clip 540 and strap attachments 550 are in accordance with other embodiments of the present disclosure.

The generally concave mask body 510 is molded of a generally gas-impermeable material, such as non-toxic medical grade plastic polymer material. In an embodiment, mask body 510 is made of silicone or polyvinyl chloride. The mask body 510 material can be transparent to allow clinicians to observe the patient's condition. The mask body 510 and connections and attachments thereto may be disposable.

The mask body 510 defines a cavity adapted to fit over the mouth and the nose of the patient. The mask body 510 optionally includes a protrusion formed on the inner-space of the mask. In an embodiment, the protrusion 590 can extend from the inner surface of the mask body to create a partial divider. The protrusion 590 is formed on the mask body 510 at a location such that the protrusion 590 at least partially separates the patient's nose and mouth. Thus, the protrusion 590 can be formed between the placement of oral aperture 560 and the top of the mask body 510. The protrusion 590 can be of various lengths, for example, between about 0.1 inches to about 3 inches. In the illustrated embodiment, the protrusion 590 is about 1.5 inches.

The peripheral edge of the mask body 510 is as described above with the peripheral edge of the mask body 210.

In various embodiments, the oxygen port 520 can be configured to accept any type of oxygen tube. In an embodiment, the oxygen port 520 is a Luer-lock port. The oxygen port 520 allows oxygen to flow from an oxygen source (not pictured) to the inner-space of the oxygen mask 500. The oxygen port 520 is formed on the upper half of the mask body 510, for example, on either side of the mask body 520. In this manner, the oxygen port 520 is located to the side of the nostrils of the patient when the oxygen mask 500 is worn allowing oxygen to be delivered to the nasal area. In a particular embodiment, the oxygen port 520 is formed on the left side of the mask (i.e., the right side of the patient). Additionally, as a Luer-lock port, the oxygen port 520 can also sample carbon dioxide using a catheter. Thus, respiration (e.g., $CO_2$ waveform) can be monitored for apneic conditions including conditions that could lead to fatal hypoxia.

One or more vent ports 530 are disposed on the bottom half of the mask body 510, allowing gases to be discharged from the oxygen mask. In various embodiments, the vent port(s) 530 can be located between one and four inches from the bottom of the mask body 510, around three inches from the bottom of the mask body 510, or around two inches from the bottom of the mask body 510. In a particular embodiment, the oxygen mask 500 includes two vent ports 530. The vent ports 530 are disposed on opposite sides of the mask body 510. The vent ports are located on the mask body 510 such that they are below the patient's mouth when the oxygen mask 500 is worn.

The vent port(s) 530 may include perforations allowing free flowing of gases. The vent port(s) 530 may be formed integrally with the molded mask body 510 or may be inserted into the mask body 510.

The oral aperture 560 is formed near the central area or upper half of the mask body 560. When the oxygen mask 500 is worn, the oral aperture 560 is located above the patient's mouth to provide access to the patient's mouth. In this matter, surgical tools can access the patient's mouth through the oral aperture 560. In an embodiment, the oral aperture 560 is formed right above the halfway line that divides the upper half and bottom half of the mask body 510. The oral aperture 560 can be any shape (e.g., generally circular, generally oval-shaped, generally rectangular), as long as the oral aperture can be formed on the mask body 510. The size of the oral aperture 560 can be between 0.1 inches and 3 inches in diameter (or by longest length). In an embodiment, the oral aperture 560 is circular in shape and about 1 inch in diameter. An optional insulator (not pictured) can be placed within the oral aperture to inhibit free flow of gas. The optional insulator can be made of any suitable material including, but not limited to, rubber, silicone and foam. The optional insulator has a hole to allow surgical tools to go through the oral aperture 560 and the optional insulator itself. In an embodiment, the optional insulator is a diaphragm with a continuous, perforable membrane.

The oxygen mask 500 can optionally include one or more nasal instrument ports 570 formed on the upper half of the mask body 510. In an embodiment, the oxygen mask 500 includes two nasal instrument ports, as illustrated in FIG. 6. In another embodiment, the oxygen mask 500 includes one nasal instrument port. Each nasal instrument port 570 is formed on the upper half of the mask body 510 such that each nasal instrument port 570 allows access to the nose and nostrils of the patient when the oxygen mask 500 is worn. In this manner, nasal instruments can access the nose and nostrils of the patient when the oxygen mask 500 is worn. Similar to the oral aperture 560, the nasal instrument port 570 can have an optional insulator. In an embodiment, the optional insulator is a diaphragm with a continuous, perforable membrane.

The oxygen mask 500 can optionally include one or more suction ports 575 formed on the mask body 510. In an embodiment, the oxygen mask 500 includes one suction port 575, as illustrated in FIG. 6. Generally, the suction port 575 is formed towards the side of the central area of the oxygen mask 500. The suction port 575 is configured to allow a suction device (not picture) to be attached to the suction port 575. In this manner, the suction device can remove liquids or other materials from the inner-space. The suction port 575 can be formed in any manner well known in the art. In an embodiment, the suction port 575 includes a diaphragm with a continuous, perforable membrane.

The oxygen mask 500 can optionally include one or more flexibility slits 580 formed on the bottom half of the mask body 510. In an embodiment, the oxygen mask 500 includes two flexibility slits 580, as illustrated in FIG. 6, but the number of slits is not critical. Therefore, a person having ordinary skill can determine the number as needed. The flexibility slits 580 can be in any shape (e.g., straight line, curved line, and V-shape). In an embodiment, the flexibility slits 580 are V-shaped. The flexibility slits 580 are formed on the bottom half of the mask body 510 below. For example, the flexibility slits 580 are formed below the oral aperture, as in the illustrated embodiment. The flexibility slits 580 can allow the mask body 510 to be more flexible.

Figure 7:
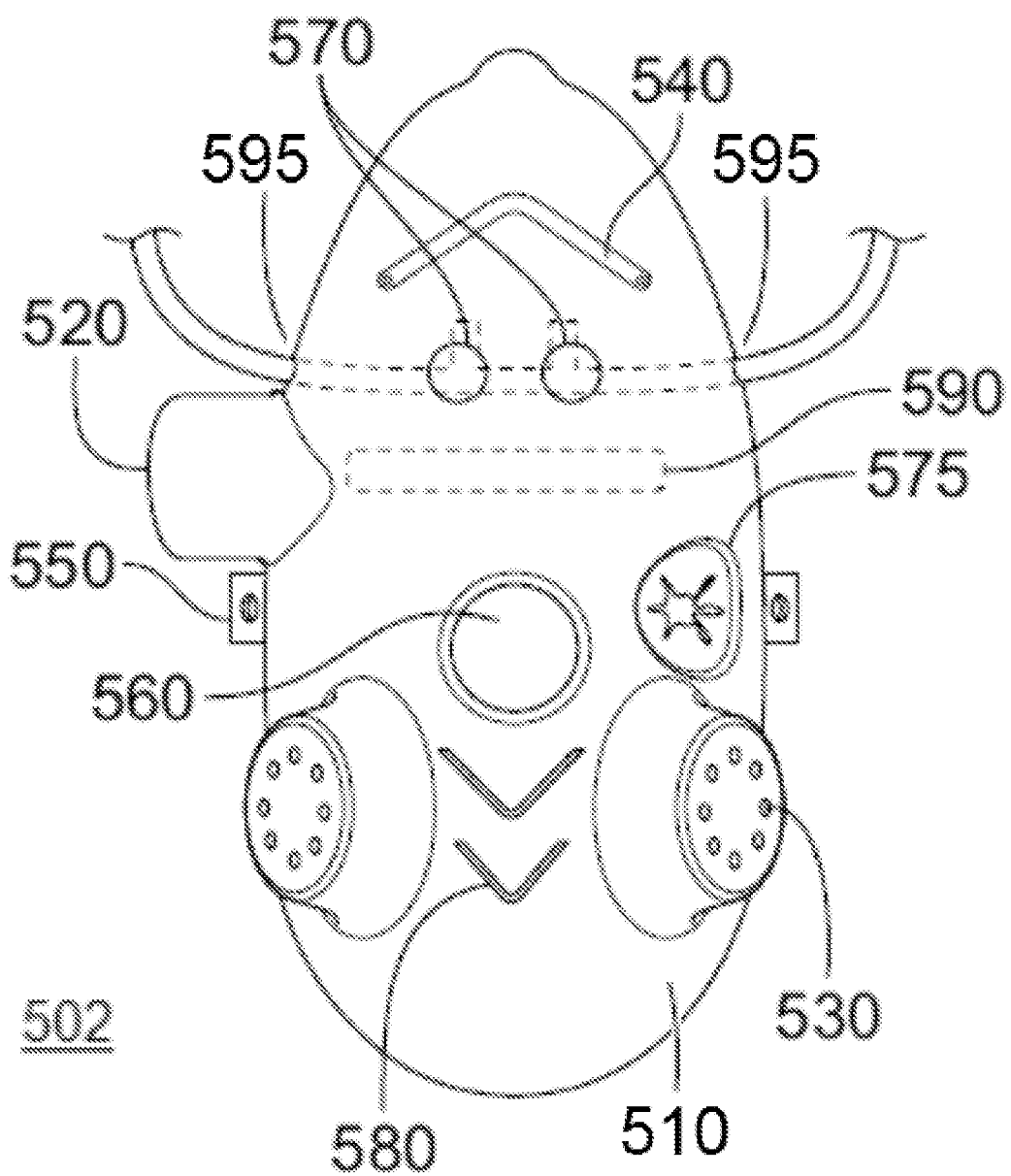
FIG. 7 shows the endoscopy mask of FIG. 6 further comprising recesses to allow nasal cannula to directly access the inner-space.

FIG. 7 illustrates another embodiment of the oxygen mask of FIG. 6. The oxygen mask 502 can include one or more optional recesses 595 formed on the peripheral edge of the mask body 510. The recesses 595 are configured and/or shaped to allow nasal cannula to directly access the nose area of the inner-space while minimizing leakage of the inner-space to the outside environment. The recess(s) 595 is/are located on the upper half of the mask body 510. The recess(s) 595 can be located between one and four inches from the bottom of the mask body 510, around three inches from the bottom of the mask body 510, or around two inches from the bottom of the mask body 510. In an embodiment, the oxygen mask 500 includes two recesses 595. The recesses 595 are disposed on opposite sides of the mask body 510. The recesses are located on the mask body 510 such that they are below the patient's mouth when the oxygen mask 502 is worn. In an embodiment, an oxygen source (not pictured) connected to the nasal cannula can alone supply oxygen to the patient. In an embodiment, an oxygen source (not pictured) connected to the nasal cannula, on conjunction with the oxygen source (not pictured) connected to oxygen port 520, can supply oxygen to the patient.

EXAMPLE

Example 1

Comparative Studies

In this example, an oxygen mask of the present disclosure is compared against nasal cannula and nasal reservoir cannula (i.e., oxymizer) for how much oxygen is delivered to the alveolar per respiratory cycle and how much oxygen is wasted.

Each respiratory cycle has three phases: inspiration, expiration, and expiratory pause. All three phases have the equal time during the respiratory cycle. Thus, each phase lasts one third of a respiratory cycle. Oxygen reaches the alveolar during the parts of the inspiration phase. During other phases of the respiratory cycle, supplied oxygen is generally wasted.

A. Nasal Cannula:

The oxygen flow rate is 4 L/minute, while the patient's respiratory rate is 15/minute. Thus, the oxygen flow rate/respiratory cycle is about 266.6 cc and the oxygen flow rate/phase is about 88.8 cc. During inspiration, ⅔ of the oxygen flow reaches the alveolar while the remaining ⅓ of the oxygen flow becomes dead space. Accordingly, about 59.2 cc of oxygen reaches the alveolar, while about 88.8 cc during expiration, about 88.8 cc during expiratory pause, and about 29.6 cc of dead space during inspiration do not reach the alveolar. Added up, about 207.2 cc of oxygen is wasted per respiratory cycle. Per minute, only about 888 cc reaches the alveolar out of a total of about 4000 cc of oxygen supplied, resulting in 77.8% wasted oxygen. With a 4 L/minute flow rate, the fraction of inspired oxygen delivered via standard nasal cannula is about 34%.

B. Nasal Reservoir Cannula (Oxymizer):

The reservoir cannula is an oxygen conserving device ("OCD"). It can store 20 ml of oxygen during exhalation and makes that oxygen available for the beginning of the next inhalation. The oxygen flow rate is 4 L/minute, while the patient's respiratory rate is 15/minute. During inspiration, ⅔ of the oxygen flow plus the 20 cc of bolus reaches the alveolar, while the remaining ⅓ of oxygen flow becomes dead space. Thus, about 59.2 cc plus about 20 cc of oxygen for a total of about 79.2 cc of oxygen reaches the alveolar. Per minute, about 1188 cc reaches the alveolar out of a total of 4000 cc of oxygen supplied, resulting in 70.3% wasted oxygen. With a 4 L/minute flow rate, the fraction of inspired oxygen delivered via reservoir nasal cannula is about 41%.

C. Oxygen Mask of the Present Disclosure:

The sealed oxygen mask saves about 88.8 cc of oxygen during expiratory pause. This 88.8 cc bolus of near 100% oxygen along with about 59.2 cc of oxygen from the oxygen flow reaches the alveolar during the early part of the inspiration phase for a total of about 148 cc of oxygen per respiration. About 2220 cc of oxygen reaches the alveolar per 4000 cc of oxygen delivered. Thus, only about 44.5% of oxygen is wasted. With the oxygen mask of the present disclosure, the fraction of inspired oxygen is approximately 60%.

Results of this comparatives study is shown in Table 1 below.

TABLE 1

Comparison of used $O_2$ per 4000 cc supplied $O_2$ and fraction of inspired $O_2$.

| | Used $O_2$ Amount (cc) | Wasted $O_2$ Amount (cc) (%) | $FiO_2$ |
|---|---|---|---|
| Nasal Cannula | 888 | 3112 (77.8%) | Approx. 34% |
| Reservoir Nasal Cannula | 1188 | 2812 (70.3%) | Approx. 41% |
| Oxygen Mask of the Present Disclosure | 2220 | 1780 (44.5%) | Approx. 60% |

The amount of used $O_2$ can be approximated by defining "X" as the amount of oxygen supplied per breathing phase of the respiratory cycle and by using the following equations (with X=88.8 cc as an example):

$X$=88.8 cc of oxygen

Nasal Cannula: (⅔)$X$=59.2 cc of used oxygen

Reservoir Nasal Cannula: (⅔)$X$+20 cc of reservoir oxygen=79.2 cc of used oxygen Mask of the Present Disclosure: (⅔)$X$+$X$=148 cc of used oxygen The $O_2$ flow rate needed to deliver $FiO_2$ to the oxygen mask of the present disclosure can be approximated as follows:

(⅔)$X$+$X$=79.2 cc $X$=47.52 cc/phase (47.52 cc/phase)(3 phases/$RR$)(15 $RR$/min)=2138.4 cc $O_2$/min Given that for 41% $FiO_2$, a reservoir nasal cannula requires an $O_2$ flow rate of 4 L/min (or 4000 cc/min). For the same oxygen delivery, the oxygen mask of the present disclosure needs only about 2.1 L/min. Therefore, the oxygen mask of the present disclosure saves more than 45% oxygen over the reservoir nasal cannula.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. An oxygen mask comprising:
 a mask body defining a cavity configured to be positioned over the mouth and nose of a patient, wherein the mask body is formed to define a reservoir for storing oxygen during expiration and the size of the reservoir is approximately 20 cc to 100 cc, and wherein the mask body is configured to be placed over a nasal cannula on the patient's face,
 an oxygen port formed on the upper half of the mask body,
 an oxygen storage tube directly coupled to a vent port at the bottom half of the mask body,
 an annular aperture formed on the mask body in a manner that the annular aperture provides mouth access of the patient, and
 a second vent port formed at a distal end of the oxygen storage tube, wherein the second vent port is formed to create an additional reservoir between the vent port at the bottom of the mask body and the second vent port.

2. The oxygen mask of claim 1, wherein the oxygen storage tube is adjustable to increase or decrease the volume of the oxygen storage tube.

3. The oxygen mask of claim 1, wherein the oxygen storage tube is configured to couple to a filter or continuous positive airway pressure machine.

4. The oxygen mask of claim 1, wherein the oxygen mask is configured to store about 75 cc of oxygen when the oxygen mask is worn.

5. The oxygen mask of claim 1, wherein the oxygen storage tube is attached to the vent port of the mask body within one inch from the bottom of the mask body.

6. The oxygen mask of claim 1, wherein the annular aperture is formed near a central area of the mask body.

* * * * *